United States Patent [19]

Kesling, Jr. et al.

[11] Patent Number: 4,996,359
[45] Date of Patent: Feb. 26, 1991

[54] PROCESS FOR THE PREPARATION OF AROMATIC BIS DIALKYL UREAS

[75] Inventors: Haven S. Kesling, Jr., Drexel Hill; Edward T. Shawl, Wallingford; John G. Zajacek, Devon, all of Pa.

[73] Assignee: Arco Chemical Technology, Inc., Wilmington, Del.

[21] Appl. No.: 167,922

[22] Filed: Mar. 14, 1988

[51] Int. Cl.$^5$ .................. C07C 275/40; C07C 273/18
[52] U.S. Cl. ........................................ 564/50; 564/48
[58] Field of Search ...................... 564/50, 53, 48, 52, 564/54

[56] References Cited

U.S. PATENT DOCUMENTS

| | | | |
|---|---|---|---|
| 2,253,528 | 8/1941 | Olin | 260/553 |
| 2,673,877 | 3/1954 | Thompson | 564/53 |
| 2,768,971 | 10/1956 | Jones | 564/53 |
| 2,993,044 | 7/1961 | Applegath et al. | 564/50 X |
| 3,386,955 | 6/1968 | Nawakowski et al. | 260/47 |
| 3,483,296 | 12/1969 | Martin | 424/322 |
| 4,303,780 | 12/1981 | Bellos | 528/367 |

FOREIGN PATENT DOCUMENTS 200441 of 1983 Czechoslovakia .
1570670 6/1969 France .
228544 of 1985 German Democratic Rep. .
47-07004 2/1972 Japan .

OTHER PUBLICATIONS

Ivanov, N. A., et al., Chemistry Department, Kalinin Agricultural Inst., 6 pgs.
Y. Shimonura, et al., Fukui Daigaku Kogakuba Kenkyu Hokoku, vol. 31, No. 2, pp. 115–127, 1983.
Sandler Organic Functional Group Prep. II, vol. 12, (1971), pp. 138–139.

Primary Examiner—Carolyn S. Elmore
Attorney, Agent, or Firm—Delbert E. McCaslin

[57] ABSTRACT

Aromatic bis (dialkyl) ureas such as the bis (dimethyl) urea of 2,4-toluenediamine are prepared by reacting an aromatic diamine with isocyanic acid (HNCO) to convert the amino groups of the diamine to urea groups (—NHCONH$_2$) to give an aromatic bis urea which is then reacted with a dialkyl amine having from 1 to 8 carbon atoms to produce the desired aromatic bis (dialkyl) urea.

11 Claims, No Drawings

PROCESS FOR THE PREPARATION OF AROMATIC BIS DIALKYL UREAS

FIELD OF THE INVENTION

The present invention relates to a process for the preparation of aromatic bis dialkyl ureas which comprises reacting an aromatic diamine with isocyanic acid to form an aromatic bis urea which is then reacted with a dialkyl amine to give an aromatic bis dialkyl urea product such as the bis (diethylureas) of 2,4-toluene diamine and 2,6-toluene diamine or mixtures thereof, which are useful for the preparation of organic isocyanates as well as for agricultural applications.

BACKGROUND OF THE INVENTION

A number of processes have been reported for the preparation of mono- and disubstituted ureas and amines as in the preparation of, for example, the bis (diethylurea) of toluenediamine by reacting toluene-2,4-diisocyanate with diethylamine described in French Pat. No. 1,570,670.

An article by N.A. Ivanov entitled "Synthesis of Substituted Ureas and Thioureas and Their Thermal Stability", Chemistry Department of the Kalinin Agricultural Institute, describes the synthesis of thioureas, monosubstituted ureas and disubstituted ureas of toluene-2,4-diamine.

German Democratic Republic Industrial Patent No. 228,544 related to the production of acyl isocyanates describes the synthesis of 1, 1'-diacyl-3, 3-dialkylureas from, for example 1, 1-dimethylurea.

Czechoslovakian Patent No. 200,441 discloses a method for the preparation of aminophenylurea by reacting phenylenediamine with one mole of cyanic acid in the presence of sodium or potassium cyanate.

An article of Y. Shimonura et al entitled "Reactions of Isocyanic Acid with Various Reagents", Fukui Daigaku Kogakuba Kenkyu Hokoku, Vol. 31, No. 2, pp 115, 1983 describes the reaction of 2-cyanoethylamine with isocyanic acid to give 2-cyanoethylurea. The synthesis of isocyanic acid from cyanuric acid by thermal decomposition is also set forth.

Applicants are not aware of any truly pertinent prior art that is deemed to be anticipatory or suggestive of the concept of the present invention.

SUMMARY OF THE INVENTION

This invention relates to a novel method for the preparation of aromatic bis dialkyl ureas which may be used in agricultural applications as insecticides and herbicides or further processed to useful isocyanate products. Aromatic diamines are reacted with isocyanic acid (HNCO) to convert the amino groups to urea groups (—NHCONH$_2$) which urea compounds are then reacted with a dialkyl amine to produce the desired aromatic bis dialkyl ureas.

The primary object of the present invention is to provide an improved process for the preparation of aromatic bis dialkyl ureas in high yield and high conversion of reactants It is another object of this invention to provide an improved reaction system for the conversion of aromatic diamines such as toluene-2,4- and 2,6-toluenediamine to aromatic bis (dialkyl) ureas.

These and other objects and advantages of this invention will become apparent from the description of the invention which follows, and from the claims.

DETAILED DESCRIPTION OF THE INVENTION

In accordance with this invention an aromatic bis (dialkyl) urea is produced having the general formula

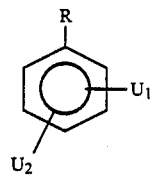

wherein R is hydrogen, a halogen, an ether group, a nitro group or an alkyl group having from 1 to 10 carbon atoms, U$_1$ and U$_2$ which may be the same or different is a —NHCONR'R" group wherein R' and R', which may be the same or different, are an alkyl group having independently from 1 to 8 carbon atoms which comprises reacting an aromatic diamine compound having the formula

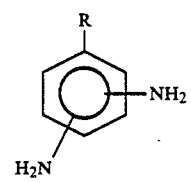

wherein R is as hereinabove described, with the R and NH$_2$ groups being at any position on the ring, with isocyanic acid at a temperature of from about $-30°$ C. to about 200° C. preferably from about $-10°$ C. to 100° C. in the presence of a solvent or mixtures of solvents, which are stable and substantially chemically inert to the components of the reaction system, to convert the amino groups of the aromatic diamine to urea groups (—NHCONH$_2$) to produce an aromatic bis urea having the formula

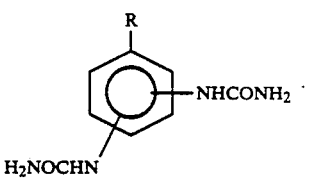

wherein R is as above described, and then reacting the aromatic bis urea thus produced with a dialkyl amine having from 1 to 8 carbon atoms in the alkyl group at a temperature of from about 50° C. to about 200° C., preferably from about 90° C. to 150° C. in the presence of a solvent or mixtures of solvents which are also stable and substantially chemically inert to the components of the reaction system and the desired aromatic bis (dialkyl) urea product recovered.

The aromatic diamines which are reacted with isocyanic acid in the process of the present invention may carry hydrogen atoms at the other ring positions, or they may be substituted by one or more groups such as an alkyl group having from 1 to 10 carbon atoms, a halogen atom, a nitro group or an ether group. Representative aromatic diamines as hereinabove described include, for example, 1,2-phenylenediamine, 4-chloro-1,2-phenylenediamine, 1,3-phenylenediamine, 1,4- phenylenediamine, 3,4-toluenediamine, 2,4-toluenediamine, 2,5-toluenediamine, 2-nitro-1-4-phenylenediamine, 4-methoxy-1,3-phenylenediamine, 4-ethoxy-1,3-phenylenediamine, and the like.

The isocyanic acid employed in the process of the present invention may be produced or generated by known methods such as the pyrolysis of urea or cyanuric acid, reaction of cyanate salts such as sodium, potassium or silver cyanate and the like with an acid such as acetic or hydrochloric acid and the like. The isocyanic acid may be generated and used in situ, or it may be distilled away from its source and used in the process of the invention as a gas or dissolved in an appropriate solvent.

In the present process the molar ratio of the (—NH$_2$) groups of the aromatic diamines to isocyanic acid is generally one to one. However, an excess of isocyanic acid of up to about 50% may be employed. Alternatively, an excess of up to about 30% (—NH$_2$) groups may be used and any unreacted or partially reacted aromatic diamines separated from the aromatic bis urea produced and recycled. In the second part of the reaction system of the instant invention the molar ratio of the dialkylamine reactant, such as dimethylamine, to the urea groups (—NHCONH$_2$) is generally one to one. However, an excess of dialkylamine of from about 10% to a ten-fold excess may advantageously be employed to drive the reaction to completion. Unreacted dialkylamine may be easily recovered by distillation for recycle in the reaction.

The dialkylamines or mixtures thereof which may be employed in the process of the invention conform to the general formula R'R"NH wherein R' and R" which may be the same or different are alkyl groups having independently from 1 to 8 carbon atoms. Representative dialkylamines include, for example, dimethylamine, diethylamine, methylethylamine, diisopropylamine, dicyclohexylamine, dibutylamine, and the like.

Solvents or mixtures of solvents which are stable and substantially chemically inert to the components of the reaction system are employed in the process steps of the present invention. Suitable solvents which may be employed include, for example, the aromatic hydrocarbons such as benzene, toluene, xylene, tetrahydronaphthalene as well as higher alkyl-substituted aromatic hydrocarbons; alkanes and substituted alkanes as well as cycloalkanes having from 5 to 20 carbon atoms such as, for example, n-hexane, n-heptane, octane, nonane, cyclohexane, dodecane, octadecane, 2-methylhexane, 2-ethylhexane, methylcyclohexane, cyclopentane and the like; halogenated or nitrated aromatic or aliphatic hydrocarbons such as, for example, methylene chloride, chloroform, carbontetrachloride, 1,2-dichloroethane, chlorobenzene, trichloroethane, tetrachloroethane, dichlorobenzene, nitrobenzene, dinitrotoluenes and the like; aromatic or aliphatic ethers such as for example, diphenylether and dibutyl ether and the like; tertiary amines such as, for example, pyridine, triethylamine, N-methylpyrrolidone and the like. Certain ketones, esters, alcohols as well as water and highly polar solvents, such as sulfolane, dimethylsulfoxide, ethylene carbonate or propylene carbonate may also be used. It is not necessary that the aromatic diamines, the reaction intermediates such as the aromatic bis ureas or the reaction products be completely miscible with the solvents at the concentrations employed. Advantage may be taken of differing solubilities of the reagents, intermediates and reaction products in the various solvents or mixture of solvents to separate the reaction components or to drive the reaction to increased product. The same solvent or mixture of solvents may be used throughout the reaction system or different solvents or solvent mixtures may be used in different steps of the process.

The intermediate aromatic bis urea obtained by the reaction of an aromatic diamine with isocyanic acid may, if desirable, be isolated from the reaction system and further processed according to the process of the invention or it may simply be carried forward as a solution or a slurry without isolation for completion of the process. In appropriate solvents, the intermediate aromatic bis urea may be essentially insoluble and the urea easily separated from unreacted aromatic diamine or partly reacted amine urea by-products by conventional techniques such as filtration, centrifugation, and the like. The separated aromatic bis urea or the crude intermediate reaction product may be reacted with a dialkyl amine to produce the desired aromatic bis dialkyl urea. The dialkyl amine reactant may be added as a gas, a liquid, a solid, or as a solution in solvent. Alternatively, the dialkyl amine may be added to the reactor along with the aromatic diamine. Ammonia generated in this part of the reaction is removed by any convenient means.

The process of the present invention may be carried out as a batch process in the same reactor employed for the first part of the reaction or as indicated hereinabove the intermediate separated and a separate reactor employed. The process may also be carried out on a semi-continuous or continuous basis and the order of addition of the materials varied to suit the particular apparatus employed.

The reactions of the present process may be carried out in any suitable reactor which is equipped with a means for temperature control and agitation. A general procedure for carrying out the process is to charge the aromatic diamine together with a solvent into the reaction vessel. The isocyanic acid is introduced into the reactor as a gas, optionally diluted with an inert gas, as a liquid, or as a solution in an appropriate solvent. Alternatively, the isocyanic acid can be charged to the reactor first together with a solvent and the aromatic diamine then added as a liquid, a solid, a solution in suitable solvent or as a slurry in a suitable inert liquid. The reaction vessel is heated or cooled as necessary to provide the desired reaction temperature for the appropriate period. Heating and/or cooling means may be employed interior or exterior of the reaction vessel to maintain temperature within desired ranges. The desired reaction product may be recovered by standard filtration and/or distillation procedure.

In the process of the present invention, the reaction of the aromatic diamines with isocyanic acid will proceed at temperatures of from about $-30°$ C. to about $200°$ C., preferably from about $-10°$ C. to about $100°$ C. Reaction time is dependent on the temperature but will generally range between about two minutes to several hours. The reaction of the intermediate aromatic bis urea and the dialkyl amines will proceed at temperatures of from about $50°$ C. to about $200°$ C., preferably from about $90°$ C. to about $150°$ C. The reaction time depends on temperature but will generally range between about 30 minutes to about 8 hours.

The process of the present invention is generally carried out at atmospheric pressure or the autogenous pressure of the reaction system, although higher pressures may be employed at the higher reaction temperatures or when the reaction temperature is above the boiling point of the solvent or dialkyl amine employed. Although subatmospheric pressure may be used there is no apparent value in employing same.

The following examples are provided to illustrate the invention in accordance with the principles of this invention and include particular features of the invention. However, the examples are not to be construed as limiting the invention in any way, it being understood that numerous variations are possible without departing from the spirit and scope of the invention.

EXAMPLE 1

A solution of 0.65 g, 5.30 mmol, 2,4-toluenediamine in 61.0 g of pyridine was charged to a 250 ml Erlenmeyer flask. The solution was stirred with a magnetic stirrer while 13.2 g of a 4.60 weight percent solution of isocyanic acid in toluene containing 0.61 g, 14.2 mmoles, of isocyanic acid was added over one minute at room temperature. Solids began to precipitate immediately on addition of the isocyanic acid solution. Solids recovered were 0.94 g. Analysis of the solids and liquid phase by high pressure liquid chromatography (HPLC) showed 97% conversion of the 2,4-toluenediamine with 85% selectivity to the 2,4-bis urea of toluenediamine as solids and 13% selectivity to amine ureas which remain in solution in the pyridine solvent. The bis urea solids were separated by filtration and suspended in 50 g 1,2-dichlorobenzene and added to a 300 ml, 3-neck round bottom flask with a magnetic stirrer, thermometer, and a condenser. Diethylamine, 2.90 g or 39.7 mmoles, was added to the flask and the mixture was heated at 130° C. for two hours. Analysis of the product by HPLC showed complete conversion of the 2,4-bis urea of toluenediamine to the bis (diethylurea) of 2,4-toluenediamine.

EXAMPLE 2

A solution of 0.80 g of 2,4-toluenediamine in 50 g of 1,2-dichloroethane was charged to a 250 ml Erlenmeyer flask containing 0.64 g 14.9 mmoles isocyanic acid dissolved in 8 g of dichloromethane. The mixture was stirred for one hour at room temperature of approximately 25° C. Solids precipitated immediately on addition of the toluenediamine solution. Analysis of the recovered solids, 1.41 g, and the solution by HPLC analysis showed 99% conversion of the toluenediamine with 98% selectivity to the bis urea of 2,4-toluenediamine The solids were suspended in 50 g 1,2-dichlorobenzene in a 300 ml, 3 neck, round bottom flask equipped with a mechanical stirrer, condenser and thermometer. Diethylamine, 4.8 g or 66 mmoles was added and the mixture was heated for two hours. Initially the temperature was limited to 120° C. by reflux of the diethylamine, but as the diethylamine was consumed, the temperature was gradually increased to 150° C. The product, the bis (diethylurea) of 2,4-toluenediamine, which was soluble in dichlorobenzene, was isolated by distilling off the solvent and unreacted diethylamine using a rotary evaporator. The solid recovered, 1.97 g, was analyzed by HPLC as 97% bis (diethylurea) of 2,4-toluenediamine and corresponded to a 91% overall yield of the bis (diethylurea) based on starting toluenediamine.

EXAMPLE 3

A 200 ml, 3 neck round bottom flask with a mechanical stirrer, condenser and thermometer was used. A solution of 3.44 g, 28 mmoles, of 2,4-toluenediamine in 100 g toluene was charged to the reactor, heated to 50° C. and then a solution of isocyanic acid, 3.44 g or 54.2 mmoles, in 87.5 g toluene added and the mixture stirred at 50° C. for 4 hours. Solids, 5.91 g, precipitated during the reaction. Dicyclohexylamine, 20 g or 110 mmoles was added to the slurry and the mixture was heated to reflux (110° C.) for 60 min. The product was isolated by distilling off solvent and unreacted amine under reduced pressure. The isolated solids, 13.5 g, contained 85% bis (dicyclohexylurea) of 2,4-toluenediamine.

EXAMPLE 4

Isocyanic acid, generated by the reaction of sodium cyanate with hydrogen chloride, was distilled away from the sodium cyanate and carried as a gas diluted with nitrogen into a 300 ml, 2-neck round bottom flask equipped with a magnetic stirrer, condenser and gas inlet tube containing 1.20 g, 10 mmoles, of 2,6-toluenediamine in 100 g o-dichlorobenzene. The reaction was held at −10° C. by a refrigerated bath. Solids precipitated in the flask. After an excess of isocyanic acid had been added, the reaction was stirred for fifteen minutes and then 1.8 g or 40 mmoles of dimethylamine was added and the mixture kept at 65° C. for 8 hours. Analysis of the product by HPLC showed an overall yield of 90% of the 2,6-bis (dimethylurea) of toluenediamine.

EXAMPLES 5-9

A number of runs were carried out according to the procedures of Example 3 employing various aromatic diamines, dialkyl amines, solvents and reaction temperatures. The product dialkyl ureas were isolated and analyzed by high pressure liquid chromatography.

The reaction conditions and results are set forth in the Table below.

TABLE

| Example No. | Aromatic Diamine (g.) | Solvent (g.) | HNCO-g. Solvent (g) | Temp. (°C.) | Time | Dialkyl Amine (g.) | Temp. (°C.) | Time | % bis (dialkyl) urea (g.) | % yield on aromatic diamine |
|---|---|---|---|---|---|---|---|---|---|---|
| 5 | 24-/2,6-TDA 80/20 (1.22) | Diphenyl Ether (100) | 1.00 Diphenyl Ether (10) | 150 | 10 min | DEA (15) | 100 | 4 hrs | 96 (3.00) | 94 |
| 6 | 24-/2,6-TDA 80/20 (12.2) | Nitro-Benzene (50) | 10 (as gas) | 30 | 1 hr. | DEA (15) | 150 | 2 hrs | 95 (30) | 89 |
| 7 | 1.3-PDA (1.08) | 1,2-Dichloro-ethane (100) | 1.00,1,2-dichloro-ethane (10) | 50 | ½ hr. | DBA (3) | 65 | 8 hrs | 85 (3.80) | 77 |
| 8 | 2,4-TDA (1.22) | Octadecane (100) | 1.00 Toluene (20) | 30 | 1 hr. | DIPA (4.2) | 110 | 3 hrs | 98 (3.60) | 94 |
| 9 | 2,4-TDA | o-Dichloro- | 0.70 (10) | 50 | 1 hr. | DEA | 125 | 2 hrs | 90 | 62 |

TABLE-continued

| Example No. | Aromatic Diamine (g.) | Solvent (g.) | HNCO-g. Solvent (g) | Temp. (°C.) | Time | Dialkyl Amine (g.) | Temp. (°C.) | Time | % bis (dialkyl) urea (g.) | % yield on aromatic diamine |
|---|---|---|---|---|---|---|---|---|---|---|
| | (1.22) | benzene (100) | | | | (3) | | | (1.50) | |

(1) PDA - Phenylenediamine
(2) TDA - Toluenediamine
(3) DEA - Diethylamine
(4) DBA - Dibutylamine
(5) DIPA - Diisopropylamine

We claim:
1. A process for the preparation of aromatic bis dialkyl ureas comprising:
   (a) reacting one or more aromatic diamines having the formula:

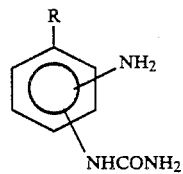

with isocyanic acid at a temperature of from about −30° C. to about 200° C. in the presence of an inert solvent to convert said aromatic diamines to one or more aromatic bis ureas having the formula:

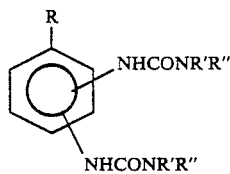

(b) reacting said aromatic bis ureas with a dialkyl amine having the formula HNR'R" at a temperature of from about 50° C. to about 200° C. in an inert solvent to produce one or more aromatic bis dialkyl ureas of the formula:

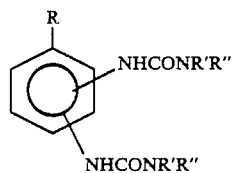

where R is hydrogen, an alkyl group having from 1 to 10 carbons, a halogen, an ether group, or a nitro group, and R' and R" are alkyl groups independently having from 1 to 8 carbons corresponding to R' and R" of said dialkylamine.

2. A process according to claim 1 wherein the temperature of reacting the aromatic diamines with isocyanic acid is in the range of from about −10° C. to 100° C.

3. A process according to claim 1 wherein the temperature of reacting said bis ureas with a dialkyl amine is in the range of from about 90° C. to 150° C.

4. A process according to claim 1 wherein the aromatic diamine is selected from the group consisting of one or more of 2,4-diaminotoluene, 2,6-diaminotoluene and 1,3 phenylene diamine.

5. A process according to claim 4 wherein the aromatic diamine is a mixture of 2,4- and 2,6-diaminotoluene.

6. A process according to claim 1 wherein the inert solvent is selected from the group consisting of 1,2-dichloroethane, diphenyl ether, nitrobenzene, toluene, octadecane, o-dichlorobenzene and pyridine.

7. A process according to claim 1 wherein the dialkyl amine reactant is selected from the group consisting of dimethyl amine, diethyl amine, dibutyl amine, diisopropyl amine and dicyclohexyl amine.

8. A process according to claim 7 wherein the dialkyl amine is dimethylamine.

9. A process according to claim 7 wherein the dialkyl amine is diethylamine.

10. A process for the preparation of a mixture of bis(dimethylureas) of 2,4- and 2,6-toluenediamine which comprises reacting a mixture of 2,4- and 2,6-toluenediamine with isocyanic acid at a temperature of from about −10° C. to 100° C. in an inert solvent to convert the 2,4- and 2,6-toluenediamine mixture to a mixture of bis ureas of 2,4- and 2,6-toluenediamine and then reacting the mixture of bis ureas of 2,4-and 2,6-toluenediamine with dimethyl amine at a temperature of from about 90° C. to 150° C. in an inert solvent and recovering the desired mixture of bis(dimethylureas) of 2,4- and 2,6-toluenediamine.

11. A process for the preparation of a bis(diethylurea) mixture of bis(dimethylureas) of 2,4- and 2,6-toluenediamine which comprises reacting a mixture of 2,4- and 2,6-toluenediamine with isocyanic acid at a temperature of from about −10° C. to 100° C. in an inert solvent to convert the 2,4- and 2,6-toluenediamine mixture to a mixture of bis ureas of 2,4- and 2,6-toluenediamine and then reacting the mixture of bis ureas of 2,4- and 2,6-toluenediamine with diethylamine at a temperature of from about 90° C. to 150° C. in an inert solvent and recovering the desired mixture of bis(diethylureas) of 2,4- and 2,6-toluenediamine.

* * * * *

UNITED STATES PATENT AND TRADEMARK OFFICE
CERTIFICATE OF CORRECTION

PATENT NO. : 4,996,359
DATED : February 26, 1991
INVENTOR(S) : Haven S. Kesling, Jr., Edward T. Shawl, John G. Zajacek It is certified that error appears in the above—identified patent and that said Letters Patent is hereby corrected as shown below:

Col. 7, lines 18-25   Delete   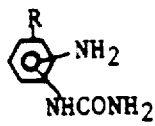   Insert   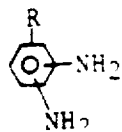

Col. 7, lines 31-38   Delete   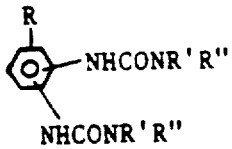   Insert   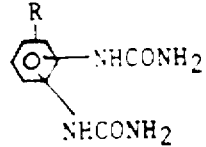

Col. 8, line 47   delete "bis(diethylurea)"

Col. 8, line 48   delete "bis(dimethylureas)" and insert therefor --bis(diethylureas)--.

Signed and Sealed this

Twenty-ninth Day of September, 1992

Attest:

DOUGLAS B. COMER

Attesting Officer

Acting Commissioner of Patents and Trademarks